United States Patent [19]

Newhouse et al.

[11] Patent Number: 5,369,022

[45] Date of Patent: Nov. 29, 1994

[54] METHOD TO IMPROVE THE PROTECTION OF CROPS FROM HERBICIDAL INJURY

[75] Inventors: Keith E. Newhouse, Bensalem; Thomas J. Schaefer, Levittown, both of Pa.

[73] Assignee: American Cyanamid Company, Wayne, N.J.

[21] Appl. No.: 123,460

[22] Filed: Sep. 17, 1993

Related U.S. Application Data

[63] Continuation of Ser. No. 682,507, Apr. 8, 1991, abandoned, which is a continuation-in-part of Ser. No. 292,207, Dec. 30, 1988, abandoned.

[51] Int. Cl.$^5$ ............................ A01H 4/00; A01C 1/06
[52] U.S. Cl. ............................ 435/172.1; 435/172.3; 47/57.6; 47/58; 800/DIG. 56; 800/DIG. 58; 504/100
[58] Field of Search ........................... 47/57.611, 58.07; 800/200, 205, 230, 250, DIG. 56, DIG. 58; 435/240.4, 172.1, 172.3; 504/100, 103

[56] References Cited

U.S. PATENT DOCUMENTS

| | | | |
|---|---|---|---|
| 3,351,525 | 11/1967 | Hodel | 514/311 |
| 3,564,768 | 2/1971 | Hoffman | 504/100 |
| 3,719,466 | 3/1973 | Anle | 504/100 |
| 3,749,566 | 7/1973 | Hoffmann | 504/108 |
| 4,127,405 | 11/1978 | Levitt | 544/211 |
| 4,343,649 | 8/1982 | Sweetser | 504/100 |
| 4,761,373 | 8/1988 | Anderson et al. | 800/200 |
| 4,810,648 | 3/1989 | Stalker | 435/240.49 |
| 4,851,031 | 7/1989 | Bellucci et al. | 504/105 |
| 5,084,082 | 1/1992 | Sebastian | 800/200 |

OTHER PUBLICATIONS

Chaleff et al. (1984) Science 224: 1443–1445.
Haughn et al. (1986) Mol. Gen. Genet. 204: 430–434.
Foreman et al. (1988) Plant Protection Quarterly 3: 78–80.
Breaux et al. (1987) J. Agric. Food Chem. 35: 474–478.

*Primary Examiner*—Che S. Chereskin
*Attorney, Agent, or Firm*—Michael P. Morris

[57] ABSTRACT

The present invention provided a method for protecting a crop from herbicidal injury by incorporating genetic resistance into the crop in combination with treating seed of the crop with a chemical safener.

9 Claims, 1 Drawing Sheet

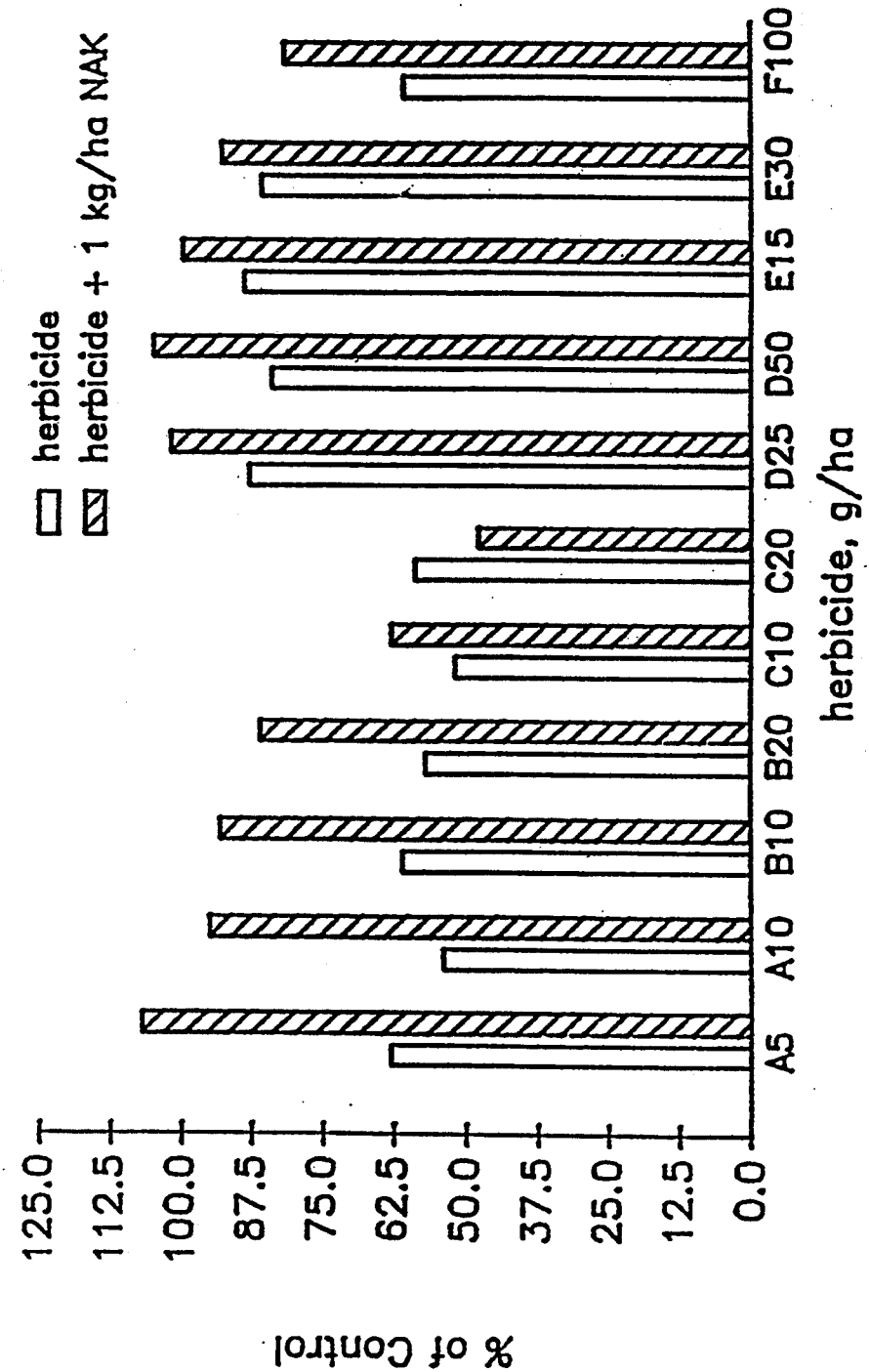

METHOD TO IMPROVE THE PROTECTION OF CROPS FROM HERBICIDAL INJURY

This application is a continuation of application Ser. No. 07/682,507, filed on Apr. 8, 1991, now abandoned, which is continuation-in-part of application Ser. No. 07/292.207, filed on Dec. 30, 1988 now abandoned.

BACKGROUND OF THE INVENTION

The invention herein described relates to a method to provide improved safety to agronomically important plants by the combination of the use of genetically imparted resistance to said plants with the use of a chemical antidote applied either to the seed of said plants or mixed with the herbicide prior to application.

A method for the production of plants, plant tissue and plant seed which contain an altered acetohydroxyacid synthase (AHAS) enzyme is described in U.S. Pat. No. 4,761,373. Plants, plant tissue and plant seeds bred to include a gene encoded with an altered AHAS enzyme also demonstrate resistance to inhibition by an herbicide at concentrations which normally inhibit the growth and development of said plants, plant tissue and plant seed.

A method to protect susceptible plants and plant seed (those without a resistance gene) is disclosed in U.S. Pat. No. 4,343,649, wherein a chemical antidote, 1,8-naphthalic anhydride, α-(cyano-methoxyimino)benzacetonitrile or N,N-diallyl-2,2-dichloroacetamide is used to protect cereal crops from injury caused by the application of certain sulfonyl-urea herbicides. U.S. Pat. No. 3,564,768, U.S. Pat. No. 3,749,566 and U.S. Pat. No. 3,719,466 disclose the use of 1,8-naphthalic anhydride as a safeners for corn, rice, wheat and grain sorghum, respectively, against injury from herbicides such as butylate, alachlor and molinate. U.S. Pat. No. 4,851,031 describes the use of quinoline derivatives such as butyl [(5-chloro-8-quinolyl)oxy]acetate as safeners for protecting cereal crops from the harmful effects of certain imidazolinone herbicides.

Now it has been discovered that the combination of introduced genetic herbicide resistance with the use of a chemical safener provides significantly enhanced protection in those cases where said genetic resistance or use of a chemical safener alone do not provide sufficient protection.

SUMMARY OF THE INVENTION

The present invention is directed to a method for protecting a crop from inhibition of growth and/or development due to a herbicidal compound by incorporating genetically imparted resistance to the herbicide in combination with treating seed of said crop with an antidotal amount of a chemical safener to the herbicide.

The genetically imparted resistance may be present within the crop species, introduced from related species, selected by tissue culture, developed by mutation breeding methods, or introduced by other gene transfer methods including, but not limited to, those involving genetic engineering and plant transformation techniques. The chemical safener may be applied to the seed of said crop or introduced into the seed zone by alternative methods including, but not limited to, spraying and granular application. Alternatively, the chemical safener can be applied as a broadcast spray to the soil and/or to the foliage of an emerged crop. The chemical safener can be applied separately, or combined with the herbicide, prior to application.

A method for the production of plants, plant tissue and plant seed which contain a resistant acetohydroxyacid synthase (AHAS) enzyme is described P. C. Anderson's U.S. Pat. No. 4,761,373 and is incorporated herein by reference thereto. Plants, plant tissue and plant seed bred to include a gene encoding a resistant ALIAS enzyme demonstrate resistance to growth inhibition by a herbicide at concentrations which normally inhibit the growth and development of said plants, plant tissue and plant seed not possessing a resistant form of AHAS.

BRIEF DESCRIPTION OF THE DRAWING

FIG. 1 is a graph of the combined effect of a chemical safener applied post-emergence and heterozygous resistant hybrid seed for increased crop protection against AHAS inhibiting herbicides.

DETAILED DESCRIPTION OF THE INVENTION

An embodiment of the invention is described wherein a herbicidal class is capable of inhibiting the AHAS enzyme in plants. Such herbicides include sulfonylureas and imidazolinones and are advantageous because they may be used at relatively low rates of application while maintaining effective control of a broad spectrum of weed species. It has now been found that crops can be protected from damage caused by this class of herbicides by incorporating a resistance gene in a heterozygous state in the crops to the herbicide in combination with treating the seed of the crops with naphthalic anhydride or a water soluble salt of naphthalic acid. The safener can be applied either as a seed treatment or as a spray applied pre-plant, pre-emergence or post-emergence to the crop.

An embodiment of this invention is hereinbelow described wherein the herbicidal agents are compounds which inhibit the AHAS enzyme in plants, such as certain sulfonyl ureas and imidazolinones, the imparted genetic resistance is the incorporation of a resistance gene in a heterozygous state in said plants, and the chemical safener includes 1,8-naphthalic anhydride and the dipotassium salt of naphthalic acid, applied either alone or in combination as a seed treatment or as a tank mixed spray either pre-plant, pre-emergence to the soil or post-emergence to said plants.

In this embodiment corn tissue cultures which are resistant to an AHAS inhibiting herbicide are selected, and plants which are resistant to the herbicide are regenerated from these cultures. These plants are cross pollinated with plants of an herbicide sensitive inbred line. Seeds obtained from the mature plants resulting from these crossings are planted, grown to sexual maturity and self-pollinated. The selfing process is repeated for a second generation. Seed is harvested from individual plants and kept separate. Homozygous resistant progeny can be identified from these plants by using a seedling assay for herbicide resistance.

The herbicide resistance gene can be introgressed by standard breeding methods to create commercial cultivars homozygous for the resistance trait. In the case wherein the plant is corn, these cultivars will be inbred lines uniformly homozygous for the resistance trait. These homozygous resistant inbred lines are then used, as either a male or female parent, in crosses with plants lacking the resistance gene to produce hybrid seed which is uniformly herbicide resistant and heterozygous for the resistance gene.

Another embodiment of the present invention is described wherein crop plants which are resistant to imidazolinone herbicides are created using a chemical mutagen. For example, seeds of the susceptible cultivar "Fidel," French winter wheat, are mutagenized following the procedure of Kueh and Bright, Planta, 153: 166-171 (1981). The wheat seeds are soaked in water for 18 hours at 5° C. and then water is bubbled through the seeds for six hours at 20° C. This is followed immediately by treatment with 1 mM sodium azide, a chemical mutagen, at pH 3 for two hours. The seeds are rinsed with water for 30 minutes and then spread in a shallow layer onto paper towels to dry. Once dry, the seeds are planted in the field. The wheat plants are grown to maturity and the mutated seed is harvested. The harvested wheat seeds are then screened for imidazolinone resistant wheat. The germination frequency of this material is 100%.

Selection and identification of the imidazolinone resistant mutants may be made by a two-step screening procedure. Generally, after chemical mutagenesis, the screening procedure involves first soaking whole, mature wheat seeds in a herbicide-containing solution for a set period of time after which the seeds are planted in a sterile soil mixture. This first step is derived from a protocol developed by Sebastian and Chaleff, Crop Science, 27: 948-952 (1987), for selection of herbicide tolerant soybean. In the second step, the soil is sprayed with a herbicide prior to the emergence of seedlings from the soil.

For example, chemically mutated wheat seeds are surface disinfested in 70% EtOH for 30 seconds followed by disinfestation in a 50% solution containing 2,625% sodium hypochlorite, with 1 to 2 drops of TWEEN-20 ® (a polyoxyethylene sorbitan monolaurate surfactant commercially available under the registered trademark of Atlas Chemical Industries) per 100 ml of solution, for 30 minutes under vacuum with gentle agitation provided by a stir plate. The seeds are then rinsed three times with sterile distilled water and placed into sterile plastic 100×15 nun Petri dishes, 250 seeds per dish. Twenty-five ml of 1000 $\mu$M or 1500 $\mu$M of a solution containing 5-ethyl-2-(4-isopropyl-4-methyl-5-oxo-2-imidazolin-2-yl)nicotinic acid commercially available from American Cyanamid Company under the registered trademark PURSUIT ®) are added to each dish and the seeds are soaked in this solution in the dark for 3 days. The seeds are then drained, blotted dry on paper towels and planted in sterile 6×8" peat flats containing METRO-MIX Growing Medium 350 ® (a mineral growth medium commercially available from W. R. Grace & Co., Cambridge, MA) with 1000 seeds planted per flat. The flats are watered and sprayed immediately with 300 g/ha or 350 g/ha of the above solution containing PURSUIT ® at a rate of about 950 L/ha.

By the method of the above-described procedure, four wheat plants are found to be resistant to the herbicide and are designated FS1, FS2, FS3 and FS4. The four mutant wheat seeds corresponding to these selections are deposited in, and readily accessible from, the American Type Culture Collection, 12301 Parklawn Drive, Rockville, MD 20852, under the accession numbers ATCC 40994 (FS1), ATCC 40995 (FS2), ATCC 40996 (FS3) and ATCC 40997 (FS4) on Mar. 28, 1991. Since the seeds from the mature inflorescence of the initial mutants retain the imidazolione resistant trait, herbicide resistant progeny may be easily obtained by conventional techniques from the mutants deposited in the American Type Culture Collection.

In a preferred embodiment of the present invention, the plant selection FS2 is utilized in combination with treating the wheat seed with the chemical safener, butyl [(5-chloro-8-quinolyl)oxy]acetate. As described above for naphthalic anhydride, the chemical safener can be applied either alone or in combination as a seed treatment or as a tank mixed spray either pre-plant, pre-emergence to the soil or post-emergence to the crops.

Compounds which are effective herbicides due to their ability to inhibit the growth and development of plants by inhibiting the AHAS enzyme can be selected from imidazolinones such as 5-ethyl-2-(4-isopropyl-4-methyl-5-oxo-2-imidazolin-2-yl)nicotinic acid, 5-methyl-2-(4-isopropyl-4-methyl-5-oxo-2-imidazolin-2yl)nicotinic acid, 2-(4-isopropyl-4-methyl -5-oxo-2-imidazolin-2-yl)nicotinic acid, methyl-2-(4-isopropyl-4-methyl-5-oxo-2-imidazolin-2-yl) nicotine acid, methyl-2-(4-isopropyl-4-methyl-5-oxo-2-imidazolin-2yl)-m-and p-toluate and 2-(4-isopropyl-4-methyl-5-oxo-2-imidazolin-2-yl)-3quinoline-carboxcylic acid; and sulfonylureas such as methyl-o-{[(4-methoxy-6-methyl-s-triazin-a-yl)carbamoyl]sulfamoyl}benzoate, ethyl-o-{[(4-chloro-6-methoxy-2-pyrimidinyl)carbamoyl)sulfamoyl}benzoate, 1-[(o-chlorophenyl)sulfonyl]-3(4-methoxy-6-methyl-s-triazin-2-yl)urea, methyl -3-{[(4-methoxy-6-methyl-s-triazin-2-yl)carbamoyl]sulfamoyl}-2-thiophenecarboxylate and methyl-o-{[3-(4,6-dimethylpyrimidin-a-yl)ureido]sulfonyl}benzoate.

For improved crop protection against damage caused by pre-emergence soil applications of AHAS inhibiting herbicides or injury caused by follow crop residues of AHAS inhibiting herbicides already present in the soil, the heterozygous resistant hybrid seed is uniformly coated with 1,8-naphthalic anhydride or butyl [(5-chloro-8-quinolyl)oxy]acetate as a 20% to 40% wettable powder formulation, preferably 20%, by mixing together 1.0 g of formulated safener and 100 g of heterozygous resistant seed. The coated seed is then planted according to agronomic conventions and the herbicide is applied to the soil before or after planting, but before crop plants emerge.

For increased crop safety against damage caused by post-emergence foliar applications of AHAS inhibiting herbicides, the heterozygous seed, coated or uncoated with the chemical safener, is planted and allowed to grow until the second to early third leaf stage. The plants are then sprayed with an aqueous solution of the dipotassium salt of 1,8-naphthalic acid or butyl [(5-chloro-8-quinolyl)oxy]acetate at a rate of about 0.35 to 1.0 kg/ha, preferably about 0.50 to 0.75 kg/ha, pre-mixed with a herbicide. The herbicide is preferably applied at a rate of about 0.005 to 0.500 kg/ha.

In order to facilitate a further understanding of the invention, the following examples are presented primarily for the purpose of illustrating more specific details thereof. Unless otherwise noted, all parts are by weight.

EXAMPLE 1

Evaluation of the combination of genetic resistance plus a chemical safener for crop protection against post-emergence application of an AHAS inhibiting herbicide The corn seeds used in this experiment are an open pedigreed hybrid (B73xMO1-7) designated as rr, and the same hybrid containing a single resistance gene (XA17), designated as Rr, the chemical safener is the dipotassium salt of 1,8-naphthalic acid (NAK), and the herbicide is 5-ethyl-2-(4-isopropyl-4-methyl-5-oxo-2-imidazolin-2-yl)nicotinic acid. The seeds are planted in six inch azalea pots with a BACCTO ® Professional Planting Mix containing sphagnum peat moss, vermiculite, perlite, limestone, superphosphate (0-46-0), calcium nitrate, potassium nitrate, and complete trace elements manufactured by Michigan Peat Company, using either two seeds (Rr) or four seeds (rr) per pot. After emergence, the plants are thinned to two plants per pot. At the 3-4 leaf stage, the plants are sprayed with aqueous solutions containing 0-0.25% NAK, 0-0.0175% herbicide and 0 5% TWEEN-20 ®, a polyoxyethylene sorbitan monolaurate surfactant of Atlas Chemical Industries, at such a rate as to provide from 0.00 to 1.00 kg/ha of NAK and from 0.00 to 0.07 kg/ha of an herbicide. Each individual treatment is replicated four times. Before applying treatments, plant heights are recorded; after treatment, the plants are placed on greenhouse benches and cared for in the usual manner commensurate with conventional greenhouse practices. Plant heights are measured and recorded at 0, 7, 12, 17 and 21 days after treatment (DAT). Mean heights are determined from these data. The results are shown in Table I.

benches and cared for in accordance with conventional greenhouse procedures. Plant heights are measured at 20 days after treatment (DAT). Mean heights are determined from these data. The results are shown in Table II.

TABLE II

Improved Protection of Heterozygous Resistant Corn From Pre-Emergence Applications of AHAS Inhibiting Herbicides Mean Plant Heights, cm

| Herbicide | Rate g/ha | NA *Seed coating | NAK Tank Mix g/ha | 20 DAT cm | % Control |
|---|---|---|---|---|---|
| 5-Ethyl-2-(4-isopropyl-4-methyl-5-oxo-2-imidazolin-2-yl)nicotinic acid$^a$ | 0 | — | 0 | 52.2 | — |
| | 0 | — | 750 | 48.3 | (93) |
| | 32 | — | 0 | 46.2 | (89) |
| | 32 | — | 750 | 50.3 | (96) |
| | 32 | + | 0 | 47.2 | (90) |
| | 63 | — | 0 | 38.2 | (73) |
| | 63 | — | 750 | 50.7 | (97) |
| | 63 | + | 0 | 48.0 | (92) |
| | 125 | — | 0 | 41.3 | (79) |
| | 125 | — | 750 | 46.3 | (89) |
| | 125 | + | 0 | 46.0 | (88) |
| | 250 | — | 0 | 29.0 | (56) |
| | 250 | — | 750 | 38.5 | (74) |
| | 250 | + | 0 | 38.0 | (73) |
| 5-Methyl-2-(4-isopropyl-4-methyl-5-oxo-2-imidazolin-2-yl)nicotinic acid$^b$ | 63 | — | 0 | 42.0 | (80) |
| | 63 | — | 750 | 45.8 | (88) |
| | 63 | + | 0 | 50.5 | (97) |
| | 250 | — | 0 | 27.8 | (53) |
| | 250 | — | 750 | 34.2 | (66) |
| | 250 | + | 0 | 42.2 | (81) |

*A seed coating treatment is designated by (+).
$^a$Expected use rate is from 50 g/ha to 100 g/ha.
$^b$Expected use rate is from 30 g/ha to 80 g/ha.

TABLE 1

Improved Protection of Corn From the Inhibition Of Growth And Development Caused By An AHAS Inhibiting Herbicide Mean plant heights, cm

| Herbicide (kg/ha) | Hybrid | NAK (kg/ha) | 0 DAT (cm) | (% of Control) | 7 DAT (cm) | (% of Control) | 12 DAT (cm) | (% of Control) | 17 DAT (cm) | (% of Control) | 21 DAT (cm) | (% of Control) |
|---|---|---|---|---|---|---|---|---|---|---|---|---|
| 0.00 | rr | 0.00 | 26 | — | 50 | — | 66 | — | 78 | — | 86 | — |
| 0.00 | Rr | 0.00 | 29 | — | 51 | — | 70 | — | 80 | — | 86 | — |
| 0.0175 | rr | 0.00 | 28 | (107) | 33 | (67) | 36 | (54) | 37 | (48) | 41 | (49) |
| 0.0175 | rr | 1.00 | 28 | (107) | 33 | (66) | 52 | (72) | 69 | (88) | 76 | (90) |
| 0.0175 | Rr | 0.00 | 28 | (96) | 39 | (72) | 60 | (84) | 72 | (89) | 80 | (93) |
| 0.0175 | Rr | 1.0 | 27 | (93) | 44 | (81) | 60 | (84) | 70 | (86) | 76 | (83) |
| 0.070 | rr | 0.0 | 26 | (100) | 30 | (57) | 30 | (46) | 0 | (0) | 0 | (0) |
| 0.070 | rr | 1.0 | 27 | (104) | 31 | (61) | 37 | (56) | 50 | (64) | 58 | (68) |
| 0.070 | Rr | 0.0 | 30 | (104) | 35 | (65) | 41 | (57) | 50 | (63) | 62 | (52) |
| 0.070 | Rr | 1.0 | 29 | (100) | 45 | (83) | 65 | (92) | 75 | (94) | 82 | (95) |

EXAMPLE 2

Evaluation of the effectiveness of the combination of heterozygous resistant corn and a chemical safener, applied as a seed coating and as a tank mix, for crop protection against pre-emergence applications of AHAS inhibiting herbicides The corn seed used in this experiment is a heterozygous resistant hybrid (B73xMO17) containing a single copy of a resistance gene (XA17). A portion of the seed is coated by mixing 100 g of seed with 1.0 g of a 20% wettable powder formulation of 1,8-naphthalic anhydride (NA). Said formulation consisting of 4% sodium lignin sulfonate, 0.8% sodium N-methyl-N-oleoyltautate, 75.2% magnesium aluminum silicate, and 20% 1,8-naphthalic anhydride. The seed and the formulated 1,8-naphthalic anhydride are placed in a bag and shaken until all the seed is uniformly coated. The coated and uncoated seeds are planted in five inch azalea pots with sterilized Princeton greenhouse soil using two seeds per pot. After planting, the pots are sprayed with an aqueous solution containing 0-0.19% of the dipotassium salt of naphthalic acid (NAK), 0-0.0625% of an herbicide, and 0.50% TWEEN-20 ®, at such a rate as to provide from 0-750 g/ha of NAK and from 0-250 g/ha of an herbicide. Each individual treatment is replicated three times. After spraying, the pots are placed on greenhouse

EXAMPLE 3

Evaluation of the effectiveness of the use of a chemical safener on heterozygous resistant corn for increased crop protection against post-emergence applications of an AHAS inhibiting herbicide The corn seed used in this experiment is a heterozygous resistant hybrid (B73xMO17) containing a single copy of a resistance gene (XA17). A portion of the seed is coated by mixing 100 g of seed with 1.0 g of a 20% wettable powder formulation of 1,8-naphthalic anhydride (NA) as described in Example 2. The coated and uncoated seeds are planted in six inch azalea pots with a BACCTO ® Professional Plant Mix using three seeds per pot. At the three leaf stage, the plants are thinned to two uniform plants per pot and are sprayed with aqueous solutions containing 0.00-0.19% of the potassium salt of 1,8-naphthalic anhydride (NAK), 0-0.0175% herbicide, and 0.5% TWEEN-20 ® at such a rate as to provide from 0 to 750 g/ha of NAK and from 0 to 62.5 g/ha of an herbicide. Each individual treatment is replicated three times. After spraying, the pots are placed on greenhouse benches and cared for in accordance with conventional greenhouse procedures. Plant heights are measured and recorded at ten days after treatment (DAT). Mean heights are determined from these data. The results are shown in Table III.

TABLE III

Improved Protection of Heterozygous Resistant Corn From Post-Emergence Applications of AHAS Inhibiting Herbicides
Mean Plant Heights, cm

| Herbicide | Rate g/ha | NA Seed coating | NAK Tank Mix g/ha | 10 DAT cm | % Control |
|---|---|---|---|---|---|
| 5-Ethyl-2-(4-isopropyl-4-methyl-5-oxo-2-imidazolin-2-yl)nicotinic acid[a] | 0 | — | 0 | 63.5 | — |
| | — | 0 | 750 | 64.8 | (102) |
| | 32 | — | 0 | 46.5 | (73) |
| | 32 | — | 750 | 58.5 | (92) |
| | 63 | — | 0 | 46.3 | (73) |
| | 63 | — | 750 | 58.8 | (93) |
| | 63 | + | 0 | 50.3 | (79) |
| 5-Methyl-2-(4-isopropyl-4-methyl-5-oxo-2-imidazolin-2-yl)nicotinic acid[b] | 32 | — | 0 | 42.5 | (67) |
| | 32 | — | 750 | 59.5 | (94) |
| | 32 | + | 0 | 48.6 | (77) |

[a]Expected use rate is from 50 g/ha to 100 g/ha.
[b]Expected use rate is from 30 g/ha to 80 g/ha.

EXAMPLE 4

Evaluation of the combined effect of a chemical safener applied post-emergence and heterozygous resistant hybrid seed for increased crop protection against AHAS inhibiting herbicides The heterozygous resistant, hybrid corn seed, is planted in six inch azalea pots using two seeds per pot with a BACCTO ® Professional Plant Mix which has been supplemented with OSMOCOTE ®, a controlled release fertilizer containing 18% nitrogen, 6% phosphoric acid, and 27% potash manufactured by the Sierra Chemical Company. The seeds are allowed to germinate and grow until the three leaf stage, and are then sprayed with an aqueous solution containing 0–0.25% of the dipotassium salt of 1,8-naphthalic acid (NAK), 0–0.0175% of an herbicide and 0.5% TWEEN-20 ® at such a rate as to provide from 0–1,000 g/ha NAK and from 0–100 g/ha of a herbicide. Each treatment is replicated three times. The pots are placed on greenhouse benches and are cared for in the usual manner commensurate with conventional greenhouse practices. Plant heights are measured at ten days after treatment (DAT). Mean plant heights are determined from these data. The results are shown in Table IV and are graphically illustrated in FIG. 1.

TABLE IV

Safening Corn Against AHAS Inhibitors Using Genetic Resistance And A Chemical Antidote
Mean Plant Heights, cm

| | Herbicide | Rate g/ha | NAK g/ha | 10 DAT cm | % Control |
|---|---|---|---|---|---|
| A | Methyl-o-{[(4-methoxy-6-methyl-s-triazin-2-yl)-carbamoyl]sulfamoyl}benzoate | 0.0 | 0.0 | 56 | — |
| | | 5.0 | 0.0 | 35 | 63 |
| | | 5.0 | 1000.0 | 60 | 107 |
| | | 10.0 | 0.0 | 30 | 54 |
| | | 10.0 | 1000.0 | 53 | 95 |
| B | Methyl-o-{[3-(4,6-dimethylpyrimidin-2-yl)ureido]- | 10.0 | 0.0 | 29 | 52 |
| | | 10.0 | 1000.0 | 35 | 63 |
| | | 20.0 | 0.0 | 33 | 59 |

TABLE IV-continued

Safening Corn Against AHAS Inhibitors Using Genetic Resistance And A Chemical Antidote
Mean Plant Heights, cm

| | Herbicide | Rate g/ha | NAK g/ha | 10 DAT cm | % Control |
|---|---|---|---|---|---|
| | sulfonyl}benzoate | 20.0 | 1000.0 | 27 | 48 |
| C | Methyl-3-{[(4-methoxy-6-methyl-s-triazin-2-yl)-carbamoyl]sulfamoyl}-2-thio-phenecarboxylate | 25.0 | 0.0 | 49 | 88 |
| | | 25.0 | 1000.0 | 57 | 102 |
| | | 50.0 | 0.0 | 47 | 84 |
| | | 50.0 | 1000.0 | 59 | 105 |
| D | Ethyl-o-{[(4-Chloro-6-methoxy-2-pyrimidinyl)carbamoyl]-sulfamoyl}benzoate | 15.0 | 0.0 | 50 | 89 |
| | | 15.0 | 1000.0 | 56 | 100 |
| | | 30.0 | 0.0 | 48 | 86 |
| | | 30.0 | 1000.0 | 52 | 93 |
| E | 1-[(o-Chlorophenyl)-sulfonyl]-3-(4-methoxy-6-methyl-s-triazin-2-yl)urea | 10.0 | 0.0 | 34 | 61 |
| | | 10.0 | 1000.0 | 52 | 93 |
| | | 20.0 | 0.0 | 32 | 57 |
| | | 20.0 | 1000.0 | 48 | 86 |
| F | 5-Ethyl-2-(4-isopropyl-4-methyl-5-oxo-2-imidazolin-2-yl)nicotinic acid | 100.0 | 0.0 | 34 | 61 |
| | | 100.0 | 1000.0 | 46 | 82 |

EXAMPLE 5

Evaluation of the effectiveness of the use of a chemical safener on imidazolinone resistant wheat for increased crop protection against post-emergence applications of an imidazolinone herbicide The wheat seeds in this greenhouse experiment are the variety "Fidel," a winter wheat variety from France and the Fidel Selection No. 2 ("FS2"), an imidazolinone-resistant wheat line containing imidazol-inone-insensitive AHAS activity The FS2 is selected from the progeny of the mutagenized seed from the cultivar Fidel. This mutant is readily obtainable from the American Type Culture Collection under the accession number ATCC 40995. The FS2 line is homozygous for the imidazolinone-resistance gene; the Fidel is homozygous for the wild type, herbicide-sensitive allele at that locus. The safener treatments in the experiment are no safener, the dipotassium salt of 1,8-naphthalic acid and butyl [(5-chloro-8-quinolyl)oxy]acetate. The herbicide is 5-ethyl-2-(4-isopropyl-4-methyl-5-oxo-2-imidazolin-2-yl)nicotinic acid.

Seeds are planted in 5-inch azalea pots filled with METRO-MIX Growing Medium 350 ®(the registered trademark of W. R. Grace & Co.). Two plants per pot are allowed to grow to 15–18 cm in height of plant growth. These plants are sprayed post-emergence with the herbicide at rates of 0, 100, 500 and 1000 g/ha in an aqueous spray solution. Pesticide treatments are sprayed at the volume of about 400 L/ha. All treatments include TWEEN-20 ® surfactant at a 0.25% v/v ratio. To each of these herbicide treatments is added either no additional safener, 1000 g/ha of the dipotassium salt of 1,8-naphthalic acid (NAK) or 750 g/ha of butyl [(5-chloro-8-quinolyl)oxy]acetate (BQA) to the spray solution. Each treatment combination is replicated three times. The experimental design is a completely randomized design.

Plant height and growth measurements are collected at 0, 14 and 28 days after treatment (DAT). Plant heights are measured by the extended leaf method. Growth is calculated as the increase in plant height after treatment application. After final measurements are made, short fresh weights are collected. Fresh weight data are measured on a per pot basis, with two plants per pot. The data from the experiment are given in the below Tables V–IX.

TABLE V

Improved Protection of Resistant Wheat From Post-Emergence Applications of AHAS Inhibiting Herbicides (Two Weeks After Treatment)
Mean Plant Heights, cm

| Herbicide Rate, g/ha | Fidel cultivar | | | FS2 selection | | |
|---|---|---|---|---|---|---|
| | without safener | with NAK | with BQA[1] | without safener | with NAK | with BQA |
| 0 | 37.5 | 36.7 | 35.1 | 27.5 | 28.7 | 26.5 |
| 100 | 17.0 | 15.8 | 32.0 | 17.8 | 24.2 | 25.3 |
| 500 | 15.7 | 15.2 | 24.8 | 16.5 | 17.8 | 26.8 |
| 1000 | 15.2 | 15.7 | 21.0 | 15.8 | 14.2 | 24.7 |

[1]BQA = butyl [(5-chloro-8-quinolyl)oxy]acetate

TABLE VI

Improved Protection of Resistant Wheat From Post-Emergence Applications of AHAS Inhibiting Herbicides (Two Weeks After Treatment)
Growth, cm

| Herbicide Rate, g/ha | Fidel cultivar | | | FS2 selection | | |
|---|---|---|---|---|---|---|
| | without safener | with NAK | with BQA[1] | without safener | with NAK | with BQA |
| 0 | 22.0 (100)[2] | 21.2 (97) | 18.2 (83) | 16.8 (100) | 15.8 (94) | 16.2 (96) |
| 100 | 0 (0) | 0 (0) | 15.5 (70) | 7.1 (42) | 13.2 (79) | 14.5 (86) |
| 500 | 0 (0) | 0 (0) | 10.5 (48) | 5.3 (32) | 4.3 (26) | 14.1 (84) |
| 1000 | 0 (0) | 0 (0) | 4.5 (20) | 3.8 (23) | 3.0 (18) | 11.7 (70) |

[1]BQA = butyl [(5-chloro-8-quinolyl)oxy]acetate
[2]The amount in parenthesis represents the percentage of growth as compared to the untreated control plants of the same genotype.

TABLE VII

Improved Protection of Resistant Wheat From Post-Emergence Applications of AHAS Inhibiting Herbicides (Four Weeks After Treatment)
Mean Plant Heights, cm

| Herbicide Rate, g/ha | Fidel cultivar | | | FS2 selection | | |
|---|---|---|---|---|---|---|
| | without safener | with NAK | with BQA[1] | without safener | with NAK | with BQA |
| 0 | 42.8 | 42.0 | 40.7 | 37.8 | 38.5 | 36.3 |
| 100 | 32.2 | 19.7 | 18.0 | 33.7 | 35.2 | 35.0 |
| 500 | 19.0 | 17.8 | 32.2 | 31.8 | 34.7 | 35.5 |
| 1000 | 17.7 | 17.5 | 20.7 | 27.7 | 26.8 | 34.7 |

[1]BQA = butyl [(5-chloro-8-quinolyl)oxy]acetate

TABLE VIII

Improved Protection of Resistant Wheat From Post-Emergence Applications of AHAS Inhibiting Herbicides (Four Weeks After Treatment)
Growth, cm

| Herbicide Rate, g/ha | Fidel cultivar | | | FS2 selection | | |
|---|---|---|---|---|---|---|
| | without safener | with NAK | with BQA[1] | without safener | with NAK | with BQA |
| 0 | 27.3 (100)[2] | 27.2 (99) | 23.8 (87) | 27.2 (100) | 26.5 (99) | 26.0 (96) |
| 100 | 2.7 (10) | 2.2 (8) | 22.3 (82) | 23.0 (85) | 24.2 (89) | 24.2 (89) |
| 500 | 3.3 (12) | 2.7 (10) | 17.8 (65) | 21.0 (76) | 21.2 (78) | 22.8 (84) |
| 1000 | 2.5 (9) | 1.8 (7) | 4.2 (15) | 15.7 (58) | 15.7 (58) | 21.7 (80) |

[1]BQA = butyl [(5-chloro-8-quinolyl)oxy]acetate
[2]The amount in parenthesis represents the percentage of growth as compared to the untreated control plants of the same genotype.

TABLE IX

Improved Protection of Resistant Wheat From Post-Emergence Applications of AHAS Inhibiting Herbicides (Four Weeks After Treatment)
Shoot Fresh Weights, g/pot

| Herbicide Rate, g/ha | Fidel cultivar | | | FS2 selection | | |
|---|---|---|---|---|---|---|
| | without safener | with NAK | with BQA[1] | without safener | with NAK | with BQA |
| 0 | 19.0 (100)[2] | 18.9 (100) | 17.4 (92) | 17.3 (100) | 16.8 (97) | 16.5 (95) |
| 100 | —* (—) | — (—) | 14.4 (76) | 9.2 (53) | 13.3 (77) | 15.5 (90) |
| 500 | — (—) | — (—) | 7.4 (39) | 7.9 (46) | 9.9 (57) | 13.8 (80) |
| 1000 | — (—) | — (—) | 1.8 (10) | 8.3 (48) | 4.1 (24) | 12.8 (74) |

*Unable to measure due to plant death and tissue deterioration.
[1]BQA = butyl [(5-chloro-8-quinolyl)oxy]acetate
[2]The amount in parenthesis represents the percentage of the fresh weight as compared to the untreated control.

We claim:

1. A method for protecting a corn crop or a wheat crop from inhibition of growth or development due to an acetohydroxyacid synthase inhibiting herbicidal compound which comprises incorporating genetically imparted resistance into the crop to the herbicide in combination with treating the crop with a chemical safener to the herbicide wherein said chemical safener is selected from the group consisting of 1,8-naphthalic anhydride, the dicationic salt of 1,8-naphthalic acid and butyl [(5-chloro-8-quinolyl)oxy]acetate.

2. The method according to claim 1, wherein the resistance is imparted by a gene encoding for an acetohydroxyacid synthase enzyme which is resistant to acetohydroxyacid synthase inhibiting herbicides.

3. The method according to claim 2, wherein the AHAS inhibiting herbicidal compound is an imidazolinone selected from the group consisting of 5-ethyl-2-(4-isopropyl-4-methyl-5-oxo-2-imidazolin-2-yl) nicotinic acid, 5-methyl-2-(4-isopropyl-4-methyl-5-oxo-2-imidazolin-2yl) nicotine acid, 2-(4-isopropyl-4-methyl-5-oxo-2-imidazolin-2-yl) 3-quinolinecarboxylic acid, 2-(4-isopropyl-4-methyl-5-oxo-2-imidazoline-2yl) nicotinic acid and the mixture of methyl-2-(4-isopropyl-4-methyl-5-oxo-2-imidazolin-2-yl)-m-toluate and methyl-2-(4-isopropyl-4-methyl-5-oxo-2-imidazolin-2-yl)-p-toluate.

4. The method according to claim 2, wherein the AHAS inhibiting herbicidal compound is a sulfonylurea selected from the group consisting of methyl-o-{[(4-methoxy-6-methyl-s-triazin-2-yl)carbamoyl]sulfamoyl} benzoate, ethyl-o-{[6-methoxy-2-pyrimidinyl)carbamoyl]sulfamoyl}benzoate, 1-[(2chlorophenyl)sulfonyl]-3-(4-methoxy-6-methyl-s-triazin-2yl)urea, methyl-3-{[(4-methoxy-6-methyl-s-triazin-2yl)carbamoyl]sulfamoyl}-2-thiophenecarboxylate and methyl-a-{[3-(4,6-dimethylpyrimidin-2-yl)ureido]sulfonyl}benzoate.

5. The method according to claim 2, wherein the gene is XA17 in a heterozygous state.

6. The method according to claim 1, wherein the dicationic salt of 1,8-naphthalic acid is selected from the group consisting of an alkali metal, an alkaline earth metal, ammonium and organic ammonium comprised of a positively charged nitrogen atom joined to form one to four aliphatic groups, each containing one to six carbon atoms.

7. The method according to claim 6, wherein the dicationic salt of 1,8-naphthalic acid is the dipotassium salt of 1,8-naphthalic acid.

8. The method according to claim 1, wherein the seed of the crop is treated by uniformly coating with a chemical safener in a 20% to 40% formulation.

9. The method according to claim 1, wherein the gene is mutated in a wheat plant and the mutant is FS1, FS2, FS3 or FS4.

* * * * *

UNITED STATES PATENT AND TRADEMARK OFFICE
CERTIFICATE OF CORRECTION

PATENT NO. : 5,369,022
DATED : November 29, 1994
INVENTOR(S) : Keith E. Newhouse; Thomas J. Schaefer It is certified that error appears in the above-identified patent and that said Letters Patent is hereby corrected as shown below:

Column 10,
Claim 3, line 36, "imidazolin-2yl) nicotine" should read --imidazolin-2-yl) nicotinic--; line 37, "-imidazolin-2-yl) 3-quinolinecarboxylic" should read -- -imidazolin-2-yl)-3-quinolinecarboxylic--; line 38, "-imidazoline-2yl)" should read -- -imidazolin-2-yl)--. Claim 4, line 46, "ethyl-o-{[6-methoxy-2-pyrimidinyl)car-" should read --ethyl-o-{[(4-chloro-6-methoxy-2-pyrimidinyl)car- --; line 47, "1-[(2chlorophenyl)sul-" should read --1-[(o-chlorophenyl)sul- --; lines 48 and 49, two occurrences, "-triazin-2yl)" should read -- -triazin-2-yl)--; line 50, "methyl-a-{[3-" should read --methyl-o-{[3- --. Claim 9, line 65, "according to claim 1" should read --according to claim 2--.

Signed and Sealed this

Tenth Day of October, 1995

Attest:

BRUCE LEHMAN

*Attesting Officer*   Commissioner of Patents and Trademarks